(12) United States Patent
Fricke et al.

(10) Patent No.: US 8,114,020 B2
(45) Date of Patent: Feb. 14, 2012

(54) SURGICAL RETRACTOR FIXING DEVICE

(76) Inventors: Helmut Fricke, Meinersen (DE); Lawrence E. Griffith, Lakeville, MN (US)

( * ) Notice: Subject to any disclaimer, the term of this patent is extended or adjusted under 35 U.S.C. 154(b) by 430 days.

(21) Appl. No.: 12/377,802

(22) PCT Filed: Aug. 17, 2007

(86) PCT No.: PCT/EP2007/007303
§ 371 (c)(1),
(2), (4) Date: Feb. 17, 2009

(87) PCT Pub. No.: WO2008/019877
PCT Pub. Date: Feb. 21, 2008

(65) Prior Publication Data
US 2010/0130828 A1    May 27, 2010

Related U.S. Application Data (60) Provisional application No. 60/838,454, filed on Aug. 17, 2006, provisional application No. 60/850,090, filed on Oct. 6, 2006, provisional application No. 60/932,127, filed on May 29, 2007.

(51) Int. Cl.
*A61B 19/00* (2006.01)
*A61B 17/02* (2006.01)
(52) U.S. Cl. ........................ 600/231; 600/227
(58) Field of Classification Search .................. 600/201, 600/226, 227, 228, 231
See application file for complete search history.

(56) References Cited

U.S. PATENT DOCUMENTS

| | | | | |
|---|---|---|---|---|
| 2,608,192 | A * | 8/1952 | Heitmeyer et al. | 600/229 |
| 3,749,088 | A | 7/1973 | Kohlmann | |
| 4,421,108 | A * | 12/1983 | Cabrera et al. | 600/234 |
| 6,017,008 | A * | 1/2000 | Farley | 248/229.21 |
| 6,254,532 | B1 * | 7/2001 | Paolitto et al. | 600/201 |
| 6,302,843 | B1 * | 10/2001 | Lees et al. | 600/228 |
| 6,530,883 | B2 * | 3/2003 | Bookwalter et al. | 600/231 |
| 6,689,053 | B1 * | 2/2004 | Shaw et al. | 600/227 |
| 6,808,493 | B1 * | 10/2004 | Bookwalter et al. | 600/233 |
| 7,156,805 | B2 * | 1/2007 | Thalgott et al. | 600/227 |
| 7,338,442 | B2 * | 3/2008 | Mulac et al. | 600/226 |

FOREIGN PATENT DOCUMENTS

FR    2239976 A1    7/1975

OTHER PUBLICATIONS

Search Report and Written Opinion of International Application No. PCT/EP07/007303.

* cited by examiner

*Primary Examiner* — Ralph Lewis
(74) *Attorney, Agent, or Firm* — Hahn Loeser & Parks LLP (57) ABSTRACT

A surgical retractor fixing device including a clamp body arranged for removably fixing the surgical retractor fixing device to a frameset that extends along a frameset longitudinal axis and that is arranged to be mounted to an operating table, a rotating body attached to the clamp body, the rotating body being pivotable around an axis of rotation, the rotating body comprising a fixing element arranged for fixing a surgical retractor, where in that the fixing element is a releasable one-way fixing element.

20 Claims, 8 Drawing Sheets

SURGICAL RETRACTOR FIXING DEVICE

This application is a national stage application of PCT/EP2007/007303 filed Aug. 17, 2007 and claims priority to and the benefit of U.S. provisional patent application 60/838,454, filed Aug. 17, 2006, U.S. provisional patent application 60/850,090, filed Oct. 6, 2006, and U.S. provisional patent application 60/932,127, filed May 29, 2007, which are incorporated herein by reference.

BACKGROUND AND SUMMARY

The invention relates to a surgical retractor fixing device, comprising: (a) a clamp body arranged for removably fixing the surgical retractor fixing device to a frameset that extends along a frameset longitudinal axis and that is arranged to be mounted to an operating table, (b) a rotating body attached to the clamp body, (c) the rotating body being pivotable around an axis of rotation, (d) the rotating body comprising a fixing element arranged for fixing a surgical retractor. According to a second aspect, the invention relates to a method of retracting structures in a surgical situation.

Originally, surgical retractors were limited to hand-held instruments with multiple curved fingers used to hold open incisions during surgical procedures. The surgeon or an assistant would hook the fingers of the surgical retractor over the edge of an incision and apply tension to hold the incision open to provide access for the surgeon to internal bodily structures.

In approximately the last two decades, surgical retractors have been developed that are secured to a surgical table or other structure to allow retraction to be accomplished without the necessity of the surgeon or an assistant constantly holding the retractor.

In general, a table rail post is the foundation of a surgical retractor system. It provides an anchor for a frameset and other hardware onto which retractor instruments and other surgical instruments may be attached. A variety of retractor instruments with variably shaped retractor fingers are used in surgery to assist the surgeon in holding a surgical incision open or to move anatomical structures out of the way. Generally, currently available surgical retractor systems use cam mechanisms or occasionally screw clamps to lock various members of the retractor system in position.

Currently available surgical retractor systems generally include round stock retractor systems and flat stock retractor systems. Flat stock retractor systems suffer the limitation that because of the rectilinear nature of the various components, the components must be joined at substantially right angles in order to interconnect. Thus, the number of orientations in which flat stock retractor systems can be assembled is limited.

Round stock retractor systems generally are preferred because they allow for the interconnection of the various retractor system components at a variety of different angles because of the ability of the round stock parts of the system to rotate relative to one another and to clamp components.

Round stock retractor systems include various rod shaped parts that, initially, were connected together by screw-threaded type clamps. As screw-threaded type clamps were used, it was discovered that there was a tendency for the screw clamps to deform the cylindrical members of the retractor system. In addition, the threads of the threaded clamps would tend to wear and fail. Further, setting up, positioning and interconnecting the parts of the retractor system often required both hands, or possibly both hands of one individual, plus an assistant to assemble the system. Over time, there has been a shift from screw-clamp connection systems to cam lock or over center lock connection Systems.

Cam lock systems generally include two interconnected clamps that are configured to grip the rod shape retractor system members and that can be adjusted in rotation relative to each other. One rod shaped component is gripped in each clamp. The two interconnected clamps are activated by some sort of actuator such as a lever which then locks the two clamps to two rod-shaped members and also simultaneously locks the two clamps relative to each other in rotation. One disadvantage of this arrangement is that when the clamps are released, they are released completely from both rod-shaped members as well as in relative rotation, requiring that the retractor system be completely repositioned and realigned before reclamping.

Surgical retractor systems are used to manipulate living tissue. Living tissue can be damaged by the application of pressure to the living tissue for too long a time. Therefore, it is recommended that during surgical procedures where mechanical retractors are used, periodically the retractors should be loosened or tension should be lessened on the retractors to allow increased blood flow to the tissue being retracted to prevent tissue hypoxia and possible necrosis, This requirement, along with the limitation of current retractor Systems, creates a dilemma for the surgical team. The surgical teams can disconnect the surgical retraction system periodically but then be required to make complete adjustments of each surgical retractor to reconnect it. Alternately, the surgical team can leave the living tissue retracted under tension for long periods of time and risk tissue damage or necrosis to the tissues being retracted. Surgical team members tend to be reluctant to disconnect and then readjust the retractor system if the readjustment is time consuming or unwieldy or if readjustment will alter the carefully positioned relationship of anatomical structures.

Another issue that arises with current round stock surgical retractor Systems arises from the fact that surgeons generally prefer to locate retractors so that they are providing retractive tension at an angle. Surgeons prefer this approach in order to move the retractor to one side of the field in which they must work so that the retractor does not interfere with their movements. When the surgical retractors are offset, quite often it is impossible to position the retractors so that the retractor is pulling completely linearly with relation to the long axis of the rod-shaped members. This imparts a torsional or rotational force to the clamps that are secured to cylindrical or rod shaped members of the retraction system. This force tends to cause the clamps of the retraction system to slip about the rods in a rotational fashion. A common response to this problem is to increasingly tighten the clamp that is applied to the rod-shaped member. Unfortunately, when tightened beyond a certain point, the clamp will tend to create deformation or galling of the rod shaped member to which it is clamped making it more difficult to adjust the system for future usage.

Another problem that arises with currently available retraction systems is that when a retractor is fixed to the system by a current clamp the joint created between components is completely locked so that the components joined are immovably fixed in all axes. Commonly, it is necessary for the surgeon or an assistant to increase or readjust retractions for certain activities. Adjusting retractions means that the surgeon or an assistant must loosen the clamp holding the retractor, reposition the retractor, and then reapply the clamp. Since the prior art clamp releases completely from two rods and in rotation simultaneously, at least two hands are required to realign and retighten the system. This can be quite awkward as there is a period of time where tension on the retractor is reduced and tissues may move in an undesirable fashion when the tension is reduced.

It is the technical problem of the present invention to mitigate at least some of the above mentioned disadvantages.

The present invention solves the problem with a surgical retractor fixing device having the features of claim 1. According to a second aspect, the invention solves the problem with a method of retracting structures in a surgical situation, the method comprising the steps: (i) mounting an anchor element to an operating table, a frameset being attached to the anchor element, (ii) attaching a surgical retractor according to the inventions to the frameset, (iii) arranging a surgical retractor relative to a human or animal patient, (iv) fixing the surgical retractor fixing device to the frameset, and (v) moving the surgical retractor, such that it retracts tissue of a patient.

The surgical retractor assembly of the present invention is arranged to be anchored to a surgical table rail or operating table, to allow retraction of anatomical structures. The surgical retractor system generally includes a retractor that can be secured in a rotating body that is further secured to a clamp body portion that, in turn, can be secured to the frameset, framing arm or other structure that, in turn can be secured to the operating table via an anchor element.

The retractor of the present invention, in one aspect of the invention, is generally conventional in structure, including curved retractor fingers secured to a shaft. The shaft may have a larger diameter portion and a smaller diameter portion.

The rotating body is rotatably securable to the clamp body.

In one embodiment of the invention, the rotating body is generally cylindrical in structure and is capable of rotation a total of about 120 degrees or even 180 degrees. The rotating body encloses or supports a fixing element arranged for fixing the surgical retractor. The fixing element may include a bind plate that is pivotally secured at one end. The bind plate includes a bind aperture which is sized to be slightly larger than the large diameter portion of the retractor. In addition, the rotating body has openings approximately aligned with the bind aperture that allow passage of the large diameter portion of the retractor through the rotating body. The bind plate is pivotable from a free-movement position where the bind plate is at a less acute angle to the shaft of the retractor to a locking position where the bind plate is pivoted to be at a more acute angle to the shaft of the retractor and thus binds the shaft of the retractor in the bind aperture preventing it from moving in one direction. Thus the retractor shaft is secured by the bind plate so that it can be withdrawn in a first direction to increase retraction but will automatically frictionally lock when moved in an opposing second direction to resist tension on the retractor.

The rotating body may include a release element such as a release button which is operably coupled to the bind plate and allows an operator to press the release button to transition the bind plate from its acute angled engagement with the shaft of the retractor to the free-movement position. Thus, retraction force can be adjusted without the necessity to release any of the other structures in the surgical retraction system. The release button may be biased toward the locked position of the bind plate by a spring or other biasing member. This arrangement ensures that a biasing force will be constantly applied to the bind plate so that the bind plate does not inadvertently slip.

The clamp body of the present invention generally includes a flex jaw and a fixed jaw and a rotating body receiver. The clamp body portion may be a substantially unitary structure that may be formed out of metal or another rigid material. In addition the clamp body may be formed out of several pieces of material such as a stainless steel. The clamp body defines a first cylindrical bore and a second cylindrical bore that are sized to receive a first and second piston therein. The first cylindrical bore and a second cylindrical bore may be substantially coaxially oriented in one aspect of the invention. The first cylindrical bore is in communication with the flex jaw portion of the clamp so that a first piston, located therein, will bear upon the flex jaw. The second cylindrical bore is in communication with a rotating body cavity within the body which is dimensioned to receive the rotating body. In one aspect of the invention, the rotating body includes a groove about the external perimeter thereof so that the second piston may bear against this groove. In one embodiment, the groove is of an appropriate circumferential length to allow the rotating body to pivot around an axis of rotation, the rotating body being pivotable having a pivotable angle range of 0 to 230 degrees. It may even be advantageous to limit the pivot angle range to 0 degree to 180 degree. In this case, the retractor is prevented from being inserted into the rotating body from the wrong side.

The rotating body may include a crescent-shaped extension extending from a bottom thereof that can be received into the rotating body cavity. In this embodiment, the second piston is sized to reach across the rotating body cavity and to bear against the concave side of the crescent extension. The body of the clamp body portion also defines a cam support cavity. The cam support cavity has a small diameter portion and a large diameter portion. The cam support cavity is in communication with both the first and second cylinder bores. In one embodiment of the invention the cam support cavity is substantially perpendicular to the first and second cylinder bores.

The present invention may also include a cam mechanism. The cam mechanism generally includes a handle such as a locking lever and a cam shaft. The handle may be pivotably mounted to the cam shaft to allow the handle to move from a position that is generally parallel to the cam shaft to a position generally at right angles to the cam shaft. The handle may also be fixedly mounted orthogonal to the cam shaft. In either case, the handle is located or locatable so as to be generally perpendicular to a rotational axis of the cam shaft.

The cam shaft generally includes a small axle portion, a dual cam, a larger axle portion, and a partial cone portion. The small axle portion is dimensioned to be rotatably received in the small diameter portion of the cam support cavity. The large axle portion is dimensioned to be received into the large diameter portion of the cam support cavity.

The dual cam portion generally includes a first cam lobe and a second cam lobe that may be located approximately 180 degrees apart. The dual cam portion may include a differential cam wherein the lobe of one cam may have a higher lift than the lobe of the other cam.

When the cam mechanism is inserted into the cam support cavity, the lobes of the two cams of the dual cam each bear upon one of the first and second pistons. In one aspect of the invention, rotation of the cam mechanism causes the lobes of the cams to force the two pistons in opposite directions. The first piston bears against the flex jaw of the clamp portion and when the piston is advanced, causes the flex jaw to move toward the fixed jaw, thus providing a clamping force that can secure the clamp to cylindrical structure of a surgical rail system.

The second piston is moved toward the rotating body. Depending upon the embodiment of the rotating body, the piston may bear against the circumferential groove, or the concave side of the crescent extension. Force applied to the second piston forces the rotating body against the interior of the rotating body cavity, thus frictionally locking the rotating body in a particular orientation when the cam mechanism is operated.

Thus, when the cam mechanism is operated, it simultaneously secures the clamp portion to a cylindrical structure of a surgical retractor support and locks the rotating body in a particular rotational orientation relative to the body of the clamp body portion. It is notable that adjustment of the retractor relative to the rotating body is independent of the operation of the cam mechanism.

According to an alternative embodiment, the clamp body may have a mouth for at least partially encompassing the frame set, the mouth being open in a mouth direction, and the clamp body comprising a locking device, the locking device having a locking rod arranged for engaging with the frameset thus fixing the clamp body to the frameset and a locking lever arranged for actuating the locking rod, the locking lever being pivotable around a locking lever swivel axis, the locking lever swivel axis being substantially perpendicular to the frameset longitudinal axis and to the mouth direction. This yields the advantage that a surgeon may first adjust and fix the surgical retractor concerning its direction relative to the frameset an afterwards fixing into the frameset.

When the retractor is inserted into the rotating body through the retractor openings and through the bind aperture of the bind plate, the spring located within the rotating body biases the bind plate to an acute angled locking orientation relative to the retractor shaft Thus, the retractor will be easily movable in a first direction relative to the rotating body and locked or jammed in motion in an opposing direction. In this way, the retractor can be withdrawn away from the patient to apply retraction force. Retraction force can be easily increased by pulling the retractor farther into the rotating body. In addition, retraction force may be reduced by pressing the push button release, thus moving the bind plate to an orientation generally perpendicular to the retractor shaft and allowing the retractor shaft to be moved in either direction as required. Release of the release button immediately locks the retractor shaft with relation to the rotating body.

BRIEF DESCRIPTION OF THE DRAWINGS

In the following, preferred embodiments of the invention are described.

DETAILED DESCRIPTION OF THE DRAWINGS

Referring to FIGS. 1 to 4, a surgical retractor fixing device 10 generally includes a retractor 12, a rotating body 14, and a clamp body 16. The clamp body 16 fixing has a locking device including a cam mechanism 18.

Figure 1:
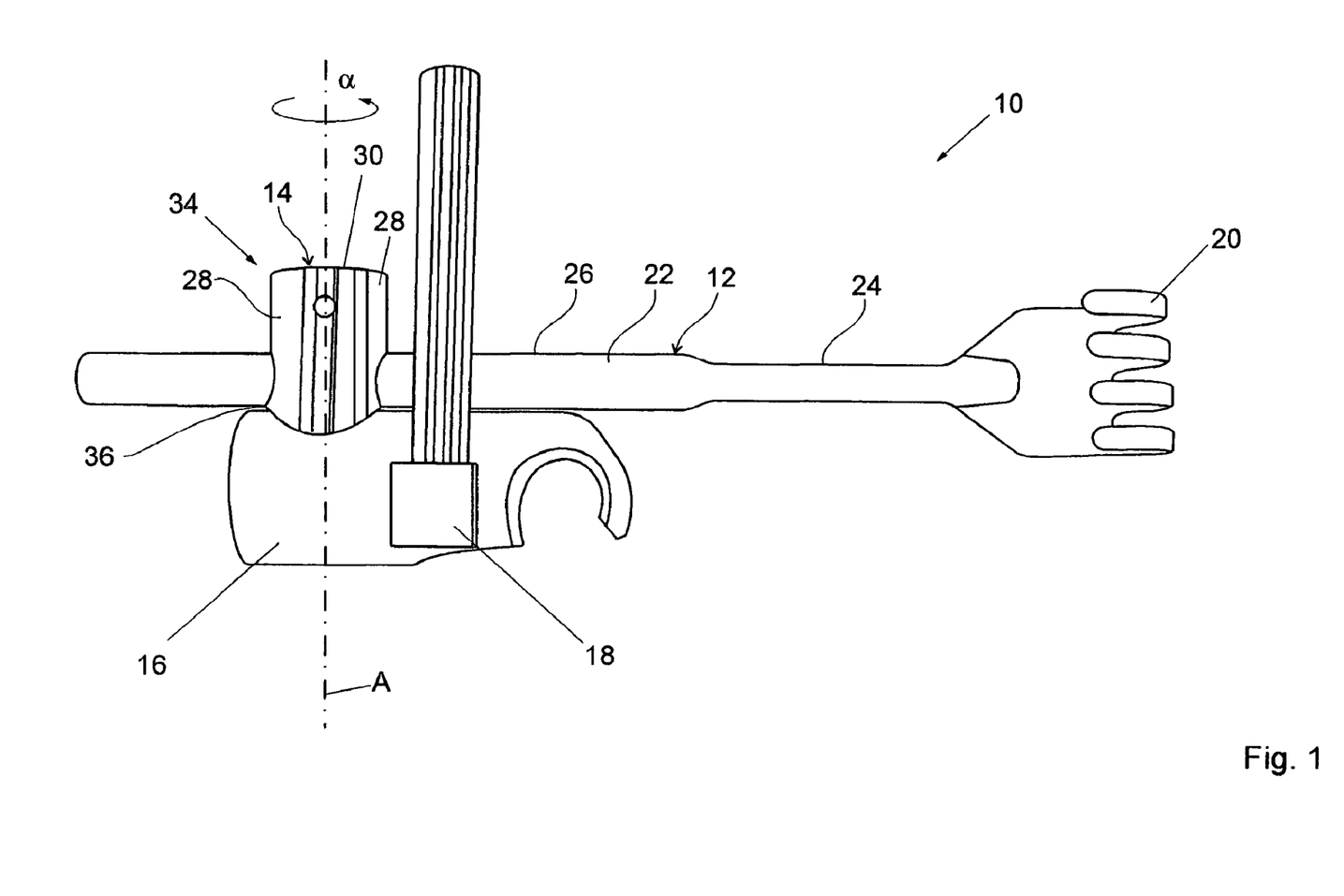
FIG. 1 is a perspective view of a surgical retractor system in accordance with the present invention.
Figure 2:
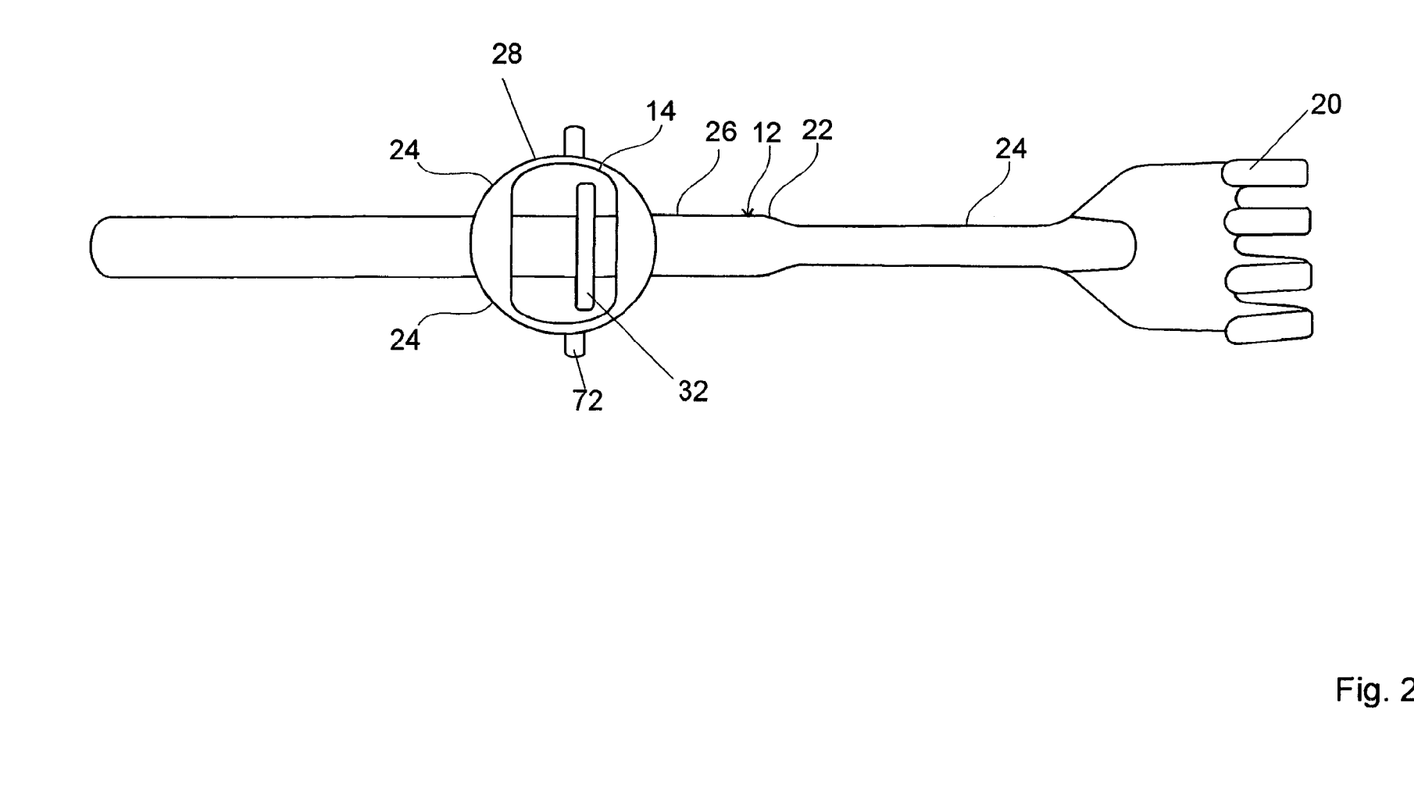
FIG. 2 is a bottom plan view of a retractor and rotating body in accordance with the present invention.

Referring to FIG. 1, retractor 12 includes fingers 20 and a shaft 22. Retractor 12 is generally formed of a biocompatible metal such as titanium or stainless steel. Other materials may be used. Fingers 20 are curved angled and generally conventional in structure. Shaft 22 includes a small diameter portion 24 and a large diameter portion 26. Fingers 20, small diameter portion 24, and large diameter portion 26 may be joined by welding or other techniques known in the arts. Rotating body 14 may be rotated around an axis of rotation A by a pivot angle α.

Figure 3:
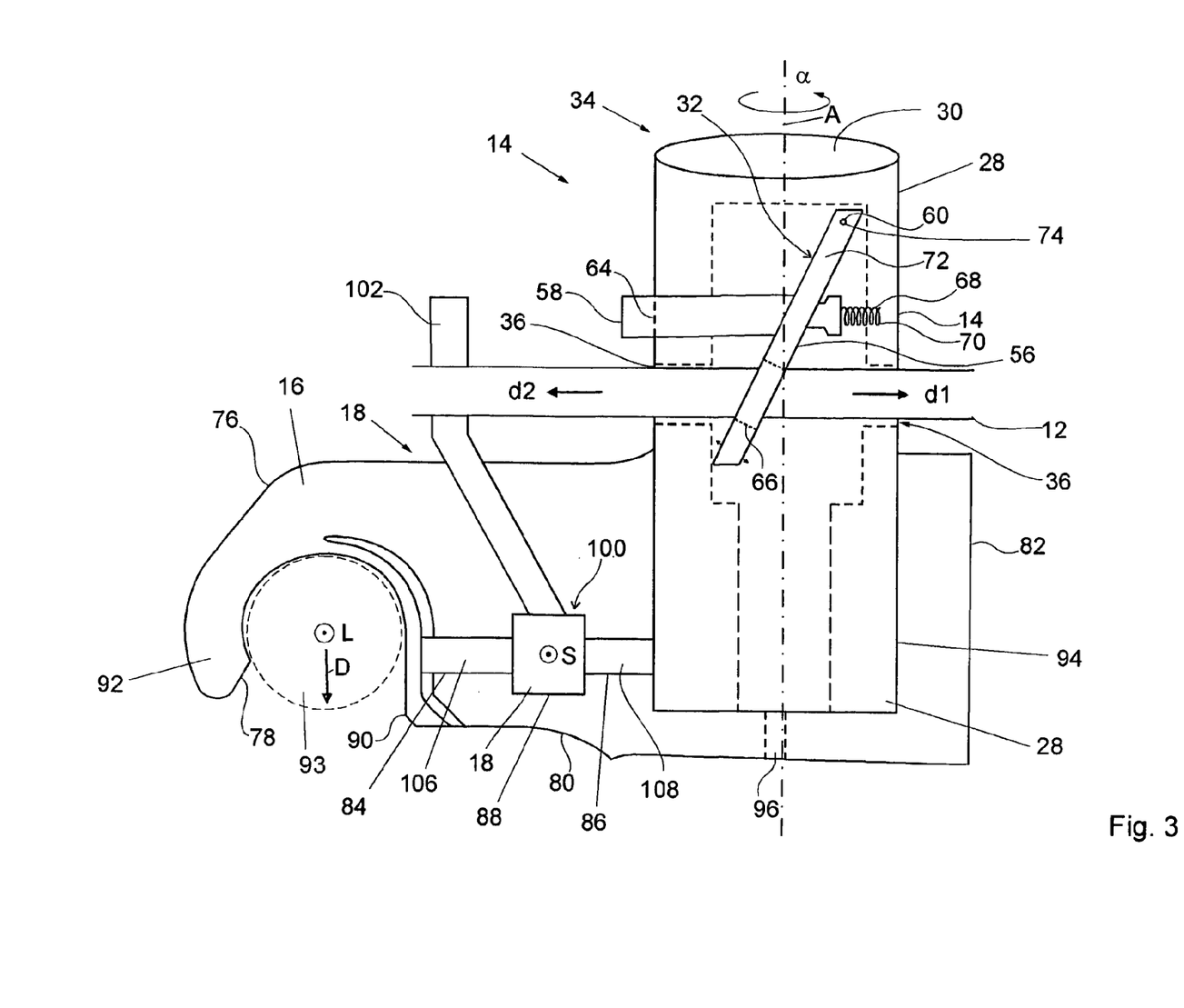
FIG. 3 is a schematic bottom plan view of a retractor and rotating body in accordance with the present invention.

Referring to FIG. 3, rotating body 14 includes a cylinder 28, a cap 30 and a bind plate assembly 32. Cylinder 28 may surround and enclose bind plate assembly 32. Cap 30 optionally closes top 34 of cylinder 28. Rotating body 14 need not be cylindrical in shape along its entire length, though the portion of rotating body 14 that interfaces with clamp body 16 should be cylindrical. Cylinder 28 is pierced by shaft holes 36. Shaft holes 36 are sized to be slightly larger than large diameter portion 26 of shaft 22. Cylinder 28 may also be pierced by release opening 38 and pivot holes 40 and pin holes 42.

Referring still to FIG. 3, a fixing element may comprise a bind plate assembly 32 generally including a bind plate 56, a release button 58 and a pivot 60. Bind plate 56 is a generally flat plate-like structure defining pin notches, a push button aperture 64 and a bind aperture 66. Bind aperture 66 is sized to be slightly larger than large diameter portion 26 of shaft 22. Release button 58 is adapted to engage push button aperture 64. Release button 58 includes biasing member 68, such as spring 70. Pivot 60 pivotally interfaces bind plate 56 to cylinder 28. Pivot 60 may take many forms. In one embodiment of the invention, pivot 60 includes pivot shaft 72 and pins 74.

Referring still to FIG. 3, clamp body 16 generally includes body 76, which, in one aspect of the invention, may be a unitary structure formed from a single piece of material. Body 76 generally defines a clamp portion 78, a cam portion 80 and a rotating body interface portion 82. Body 76 defines a first cylinder bore 84, a second cylinder bore 86 and a cam support cavity 88. First cylinder bore 84 and second cylinder bore 86 are in communication with cam support cavity 88. First cylinder bore 84 is also in communication with clamp portion 78.

Clamp portion 78, as depicted in FIG. 3, includes flex jaw 90 and fixed jaw 92. Clamp portion 78 has a mouth direction D and is sized to grip a cylindrical surgical frameset 93 that extends along a frameset longitudinal axis L if inserted in mouth direction D. Flex jaw 90 may be formed, for example, by cutting clamp portion as shown. The second cylinder bore 86 is in communication with a rotating body cavity 94. Rotating body cavity 94 may also communicate with a drain hole 96.

Cam support cavity 88 generally defines a small diameter portion acting as bearing for a cam shaft and a large diameter portion. Cam mechanism 18 comprises a first piston 106 and a second piston 108 that are actuated by a cam (not shown) that is attached to a handle 102.

Handle 102 may be fixedly or pivotably mounted to the cam shaft. If pivotably mounted, handle 102 pivots on an locking lever swivel axis S generally perpendicular to a long axis of the cam shaft. Cam shaft defines a small axle, a large axle and a dual cam. Dual cam generally includes first a cam and a second cam. First cam and second cam are generally 180 degrees opposed to one another though they may be oriented otherwise. The cam shaft may include a differential cam. In the differential cam, the first cam has a lift different from the second cam. The cam shaft may also define a partial cone portion. First piston 106 travels within first cylinder bore 84. Second piston 108 travels within second cylinder bore 86. The cam shaft fits into cam support cavity 88.

Still with reference to FIG. 3, in operation, when the cam shaft is turned, first cam bears against first piston 106, which in turn bears against flex jaw 90. The rotation of cam shaft forces flex jaw 90 toward fixed jaw 92, thus providing a clamping action on a cylindrical surgical retractor support structure 93 placed within flex jaw 90 and flex jaw 92. Simultaneously, the turning of the cam shaft causes second cam to bear against second piston 108, which in turn bears against a portion of cylinder 28. In one embodiment of the invention, second piston 108 bears against groove 44 of cylinder 28, thus forcing cylinder 28 against the interior of rotating body cavity 94, thus locking rotating body 14 rotationally relative to clamp body 16.

Retractor 12 is inserted into rotating body 14 through shaft holes 36 and also through bind aperture 66 of bind plate 56. The biasing of bind plate 56 by spring 70 or other biasing member 68 tends to force bind plate 56 to a position at an acute angle d relative the long axis of shaft 22 of retractor 12. This allows the fixing element to be releasable one-way as the shaft 22 of retractor 12 may be moved relatively freely with some frictional resistance in a first direction d1 while locking shaft 22 against movement in a second direction d2. This allows for easy adjustment of retractor 12 to increase retraction tension on a bodily structure without the need to release the locking of either rotating body 14 or clamp portion 78.

If it is desired to reduce retracting tension on retractor 12, an operator can press release button 58 which directs bind plate 56 to a position generally perpendicular to shaft 22 which allows the movement of retractor 12 in either direction. As soon as release button 58 is released, retractor 12 is again locked in tension but movable in compression.

Figure 4:
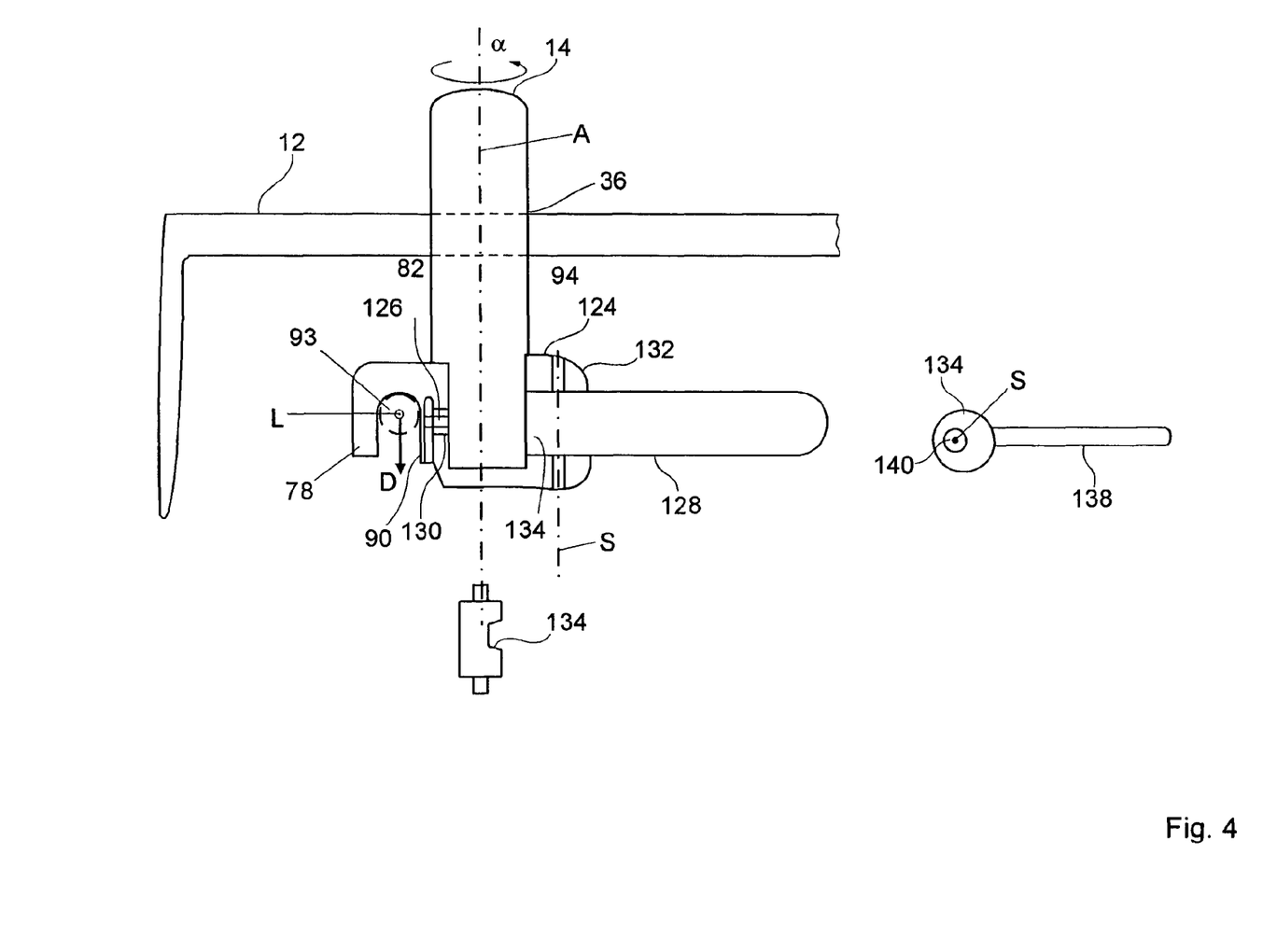
FIG. 4 is a schematic sectional view of an embodiment of the invention.

Referring to FIG. 4, in another embodiment, clamp body 16 generally includes a clamp portion 78, a rotating body interface portion 82 and a locking lever portion 124. Clamp portion 78 and rotating body interface portion 82 are generally similar to that described above. Locking lever portion 124 generally includes a connecting rod 126 and locking lever 128. In this embodiment, clamp body 16 defines connecting rod passage 130 and locking lever yoke 132.

Locking lever 128 generally includes an eccentric 134, a notch 136, a handle 138 and a shaft 140. Shaft 140 is supported in locking lever yoke 132 so that eccentric 134 and handle 138 rotate around shaft 140 thus defining locking lever swivel axis S. As handle 138 is turned, eccentric 134 is shifted between bearing against rotating body 14 to not touching rotating body 14. In this aspect of the invention, rotating body 14 is free to shift slightly within rotating body cavity 94 to the vicinity of flex jaw 90.

When eccentric 134 is rotated about shaft 140 to bear on rotating body 14, rotating body shifts within rotating body cavity 94 towards flex jaw 90 and bears against connecting rod 126, which in turn bears against flex jaw 90, thus, moving flex jaw 90 toward fixed jaw 92.

Figure 5:
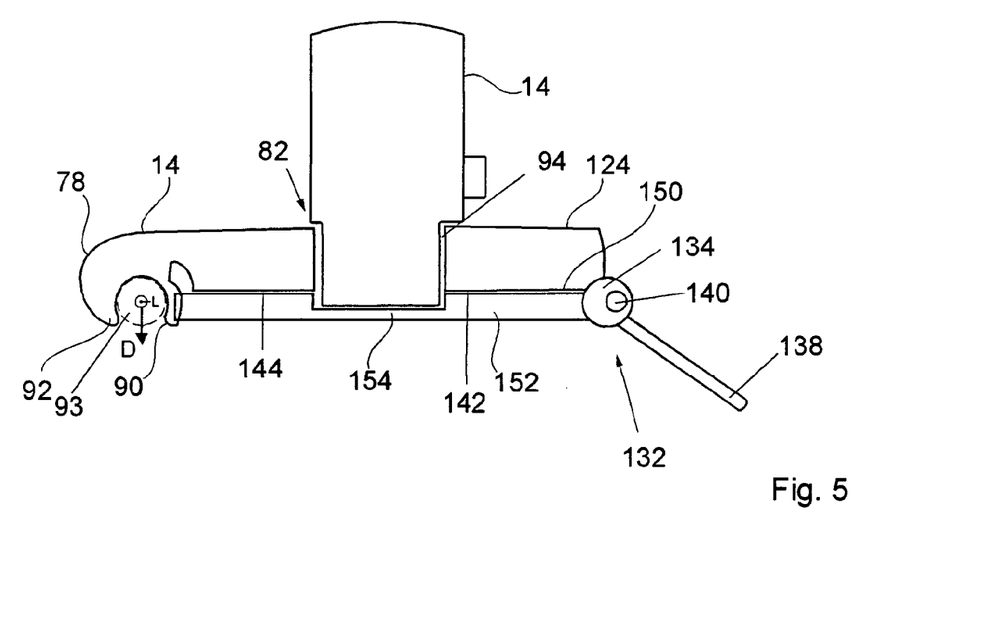
FIG. 5 is a schematic sectional view of another embodiment of the invention.
Figure 6:
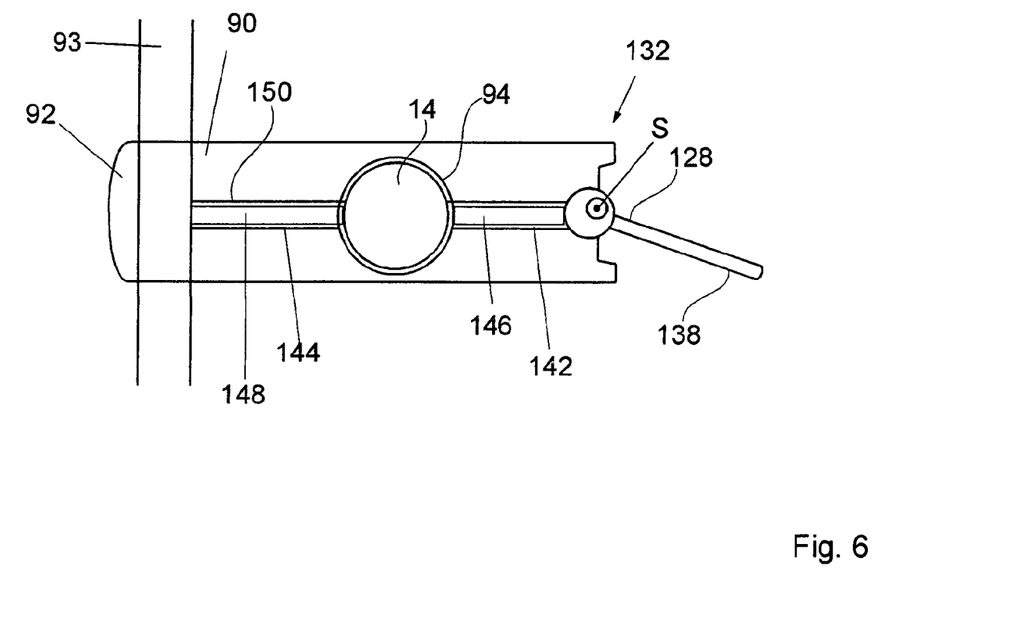
FIG. 6 is a schematic sectional view of yet another embodiment of the invention.

Referring to FIGS. 5 and 6 alternative embodiments of the surgical retractor fixing device 10 are depicted. The clamp body 16 is generally similar to the above described embodiments including clamp portion 78 and rotating body interface portion 82. In this embodiment, clamp body 16 defines first connecting rod passage 142 and second connecting rod passage 144. First connecting rod passage 142 communicates between locking lever yoke 132 and rotating body cavity 94. Second connecting rod passage 144 communicates between rotating body cavity 94 and flex jaw 90. As shown in FIG. 6, the fixing device may include first connecting rod 146 and second connecting rod 148. First connecting rod 146 is slidably positioned in first connecting rod passage 142. Second connecting rod 148 is positioned in second connecting rod passage 144.

In this embodiment, in operation, when locking lever 128 is rotated about shaft 140, and thus about locking lever swivel axis S, eccentric 134 bears against first connecting rod 146. First connecting rod 146 bears against rotating body 14, which in turn bears against second connecting rod 148. Second connecting rod 148 then bears against flex jaw 90 to move flex jaw 90 toward fixed jaw 92. Thus the rotation of rotating body 14 is stopped while flex jaw 90 is forced toward fixed jaw 92 to fit clamp body 16 against a surgical frameset.

Referring to FIG. 5, clamp body 16 defines notched connecting rod passage 150. Notched connecting rod passage 150 communicates between locking lever yoke 132 and flex jaw 90 while also passing partially through rotating body cavity 94. Notched connecting rod 152 is slidably positioned in notched connecting rod passage 150.

In this embodiment of the invention, in operation, when locking lever 128 is turned to rotate eccentric 134 about shaft 140, eccentric 134 bears against notched connecting rod 152 forcing toward flex jaw 90. As notched connecting rod 152 is moved, notched portion 154 of notched connecting rod 152 bears against rotating body 14, thus frictionally securing rotating body 14 in position. Simultaneously notched connecting rod 152 bears against flex jaw 90 thus forcing flex jaw 90 toward fixed jaw 92. Thus, the operation of locking lever 128 secures rotating body 14 and flex jaw 90 simultaneously.

Notably, the above described three embodiments eliminate all interference between locking lever 128 and retractor 12 thus allowing retractor 12 positioned in rotating body 14 to rotate 360° without mechanical obstruction by locking lever 128. This is a distinct advantage in allowing for free positioning of retractors on surgical rails or frames. Alternatively, rotations limiting elements may be provided to limit the pivot angle α (c.f. FIG. 1) of rotating body 14.

Figure 7A:
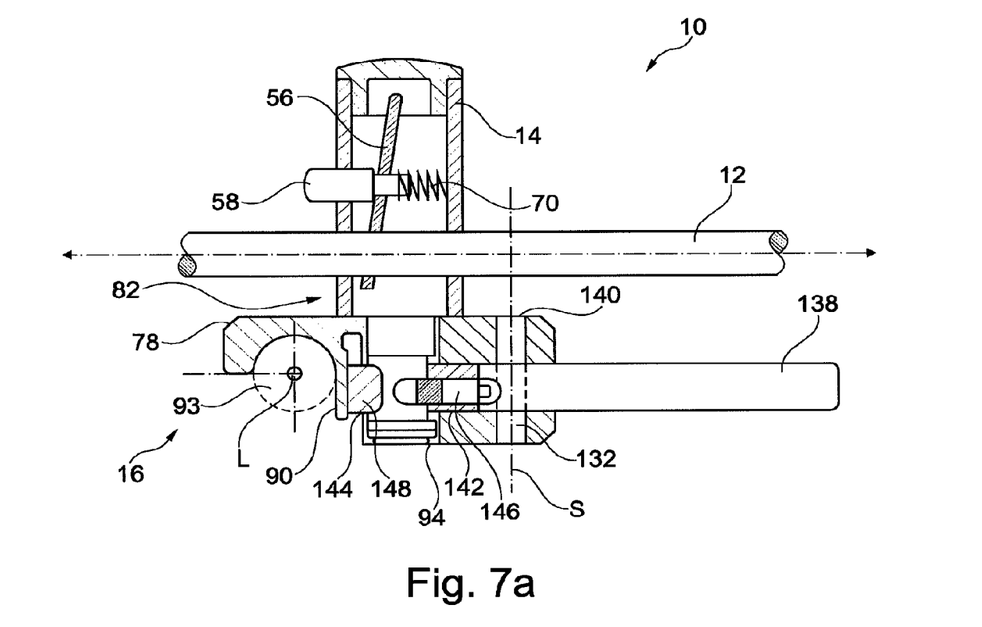
FIGS. 7a and 7b are schematic sectional views of yet another embodiment of the invention.
Figure 7B:
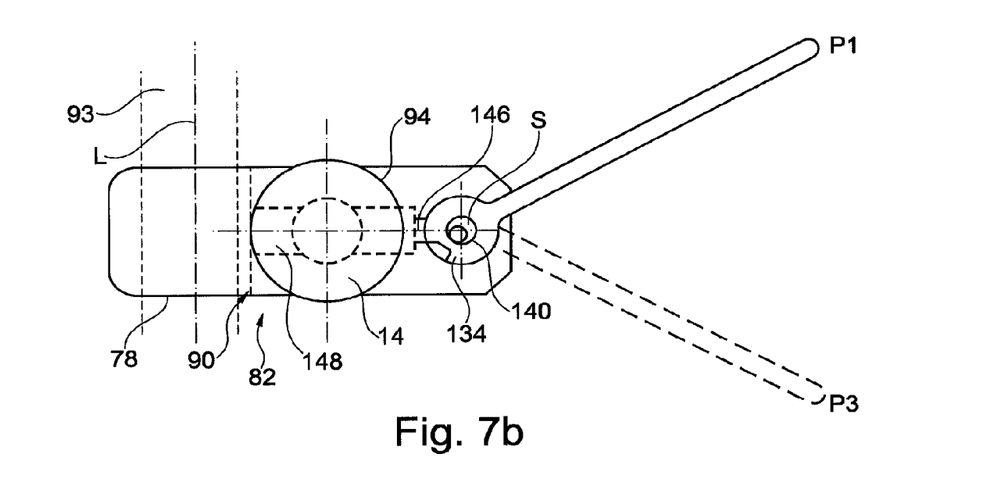

FIGS. 7a and 7b show another embodiment of the present invention. Like parts are referred to as in the figures above.

Figure 8:
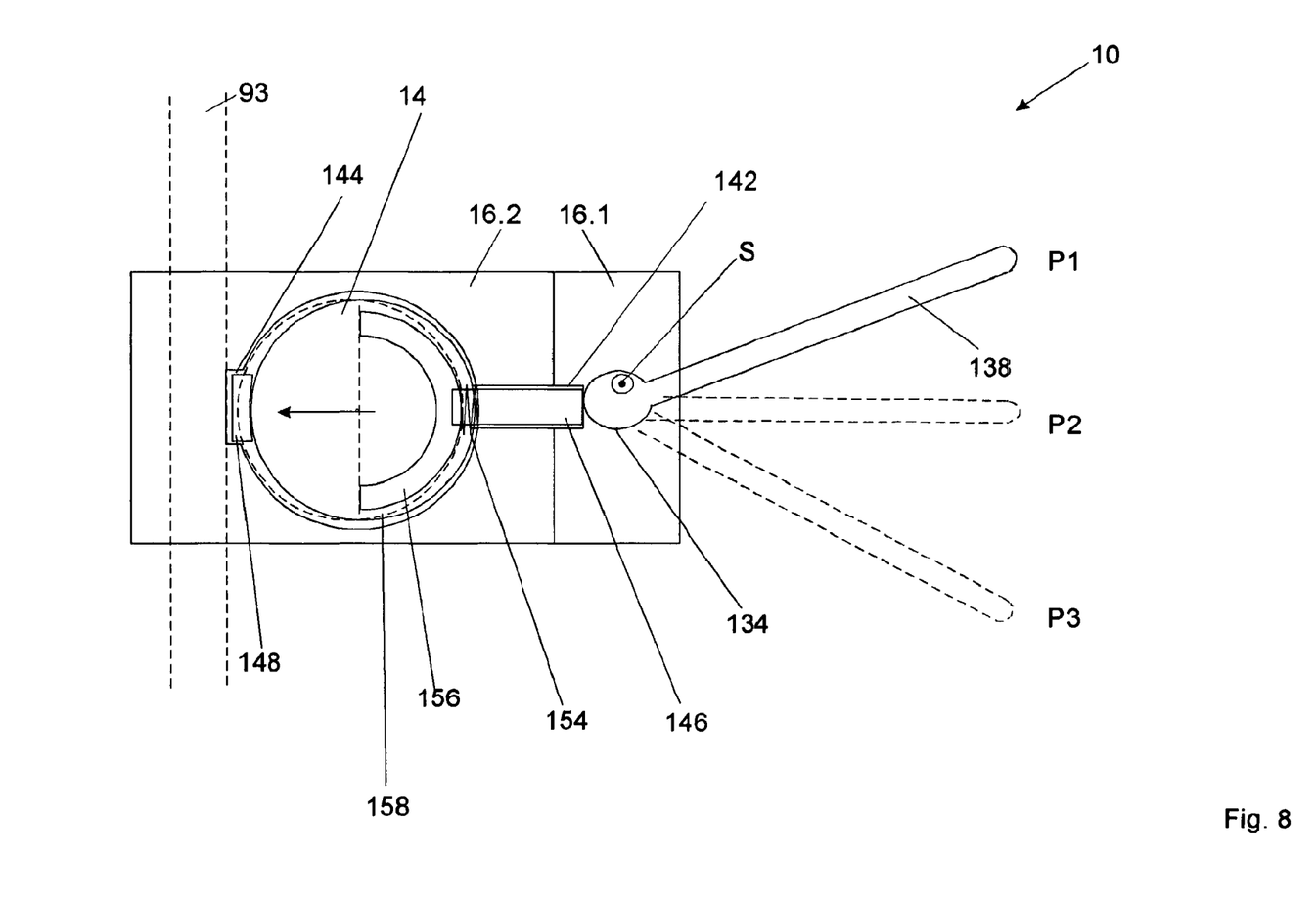
FIG. 8 is a schematic sectional view of yet another embodiment of the invention.

Referring to FIG. 8, the clamp body 16 of surgical retractor fixing device 10 comprises a first clamp body part 16.1 and a second clamp body part 16.2 that are joined together, e.g. by screws (not shown). The first connecting rod 146 comprises an elastic element 154, e.g. a spring. Spring 154 is attached to a semi-circular element 156. The semi-circular element 156 is located within a circular notch 158 in the rotating body 14. When handle 138 is moved from a first position P1 to a second position P2, eccentric 134 pushes against first connecting rod 146 and biases spring 154 and semi-circular element 156 against rotating body 14. Due to friction between semi-circular element 156 and rotating body 14, rotating body 14 is pre-fixed relative to clamp 16.2. At the same time, rotating body 14 exerts a force on second connecting rod 148 that is weak enough, so that clamp body 16 may still be moved along frameset 93 in direction of frameset longitudinal axis L.

When handle 138 is moved from position P2 to position P3, the pressure exerted by spring 154 is sufficient to clamp rotating body 14 to clamp body 16.2 and clamp body 16.2 to frameset 93.

Figure 9:
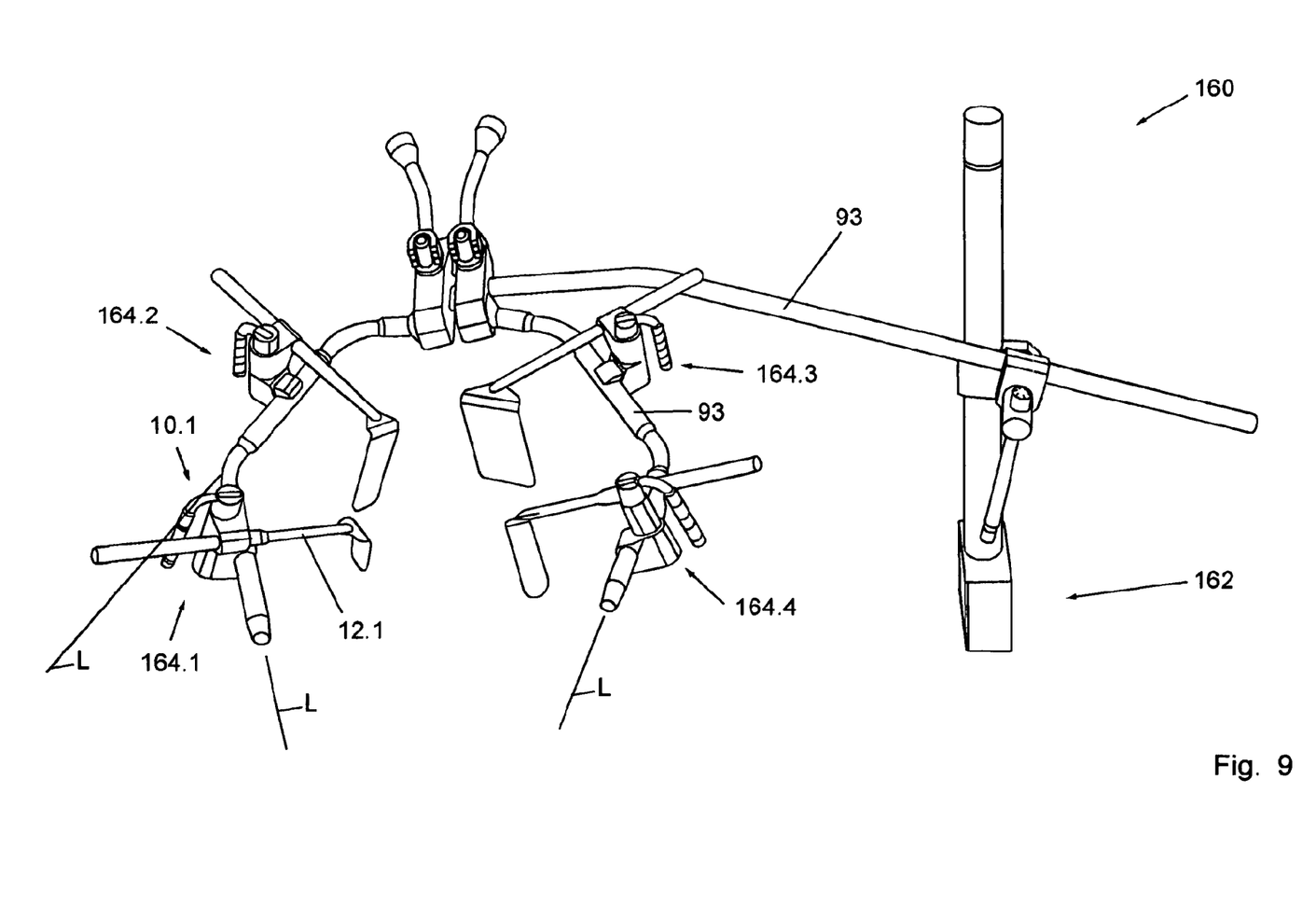
FIG. 9 depicts a surgical retractor assembly according to the invention.

FIG. 9 shows a surgical retractor assembly 160 comprising a frameset 93 and an anchor element 162 for fixing the frameset 93 to an operating table (not shown). Several surgical retractor systems 164.1, 164.2, 164.3, and 164.4 are attached to frameset 93. Each surgical retractor system 164 comprises a surgical retractor fixing device 10 and a retractor 12.

In a surgical situation, a patient is put on a not shown operating table and the anchor element 162 is mounted to the operating table. Then, several surgical retractor fixing devices are attached to the frameset 93 and arranged by a surgeon relative to the human or animal patient. The surgical reflector fixing devices 10 are the fixed to the frameset such that the respective retractor is located within an incision or open wound. To hold the incision open, the surgical retractors are then moved such that they retract the respective tissue or organs.

REFERENCE NUMERALS 10 surgical retractor fixing device
12 retractor
14 rotating body
16 clamp body
18 cam mechanism
20 finger
22 shaft
24 small diameter portion
26 large diameter portion
28 cylinder
30 cap
32 bind plate assembly
34 top (of cylinder 28)
36 shaft hole
38 release opening
40 pivot hole
42 pin hole
56 bind plate
58 release button
60 pivot
62 pin notch
64 push button aperture
66 bind aperture
68 biasing member
70 spring
72 pivot shaft
74 pin
76 body
78 clamp portion
80 cam portion
82 rotating body interface portion
84 first cylinder bore
86 second cylinder bore
88 cam support cavity
90 flex jaw
92 fixed jaw
93 frameset
94 rotating body cavity
96 drain hole
102 handle
106 first piston
108 second piston
122 partial cone portion
124 locking lever portion
126 connecting rod
128 locking lever
130 connecting rod passage
132 locking lever yoke
134 eccentric
136 notch
138 handle
140 shaft
142 first connecting rod passage
144 rod passage
146 first connecting rod
148 second connecting rod
150 connecting rod passage
152 connecting rod
154 elastic element
156 semi-circular element
158 circular notch
160 surgical retractor assembly
162 anchor element
164 surgical retractor system
α pivot angle
A axis of rotation
D mouth direction
L frameset longitudinal axis
S locking lever swivel axis

What is claimed is:

1. A surgical retractor fixing device comprising:
    a clamp body (16) arranged for removably fixing the surgical retractor fixing device (10) to a frameset (93) that extends along a frameset longitudinal axis (L) and that is arranged to be mounted to an operating table, and
    a rotating body (14) attached to the clamp body (16) being pivotable around an axis of rotation (A), the rotating body (14) comprising a fixing element (32) arranged for fixing a surgical retractor (12), where the fixing element is a releasable one-way fixing element (32), the rotating body (14) having a linear guide (36) transverse to the axis of rotation (A) for guiding the surgical retractor (12), and the fixing element (32) comprising a bind plate (56), the bind plate (56)
        being pivotably attached to the rotating body (14) and operable to at least partially surround the surgical retractor (12),
        the bind plate (56) pivoting with movement of the surgical retractor (12) in a first linear direction (d1) enabling movement of the surgical retractor (12) in the first linear direction along the linear guide (36), and
        the bind plate (56) resisting movement of the surgical retractor (12) in a second direction (d2) opposite the first linear direction.

2. The surgical retractor fixing device (10) according to claim 1, the axis of rotation (A) extending substantially perpendicular to the frameset longitudinal axis (L).

3. The surgical retractor fixing device according to claim 1, the fixing element (32) comprising a release element (58) pivoting the bind plate (56) enabling the surgical retractor moving in the first and second directions.

4. The surgical retractor fixing device according to claim 1, the rotating body (14) being pivotable having a pivot angle range of less than 230°.

5. The surgical retractor fixing device according to claim 1,
    the clamp body (16) having a mouth for at least partially encompassing the frameset (93), the mouth being open in a mouth direction (D), and
    the clamp body (16) comprising a locking device, the locking device having
        a locking rod (106) arranged for engaging with the frameset (93) thus fixing the clamp body (16) to the frameset (93) and
        a locking lever (128) arranged for actuating the locking rod piston (106), the locking lever (128) being pivotable around a locking lever swivel axis (S),
        the locking lever swivel axis (S) being substantially perpendicular to the frameset longitudinal axis (L) and to the mouth direction (D).

6. The surgical retractor fixing device according to claim 5, where the locking rod comprises a first connecting rod (146) and a second connecting rod (148), the first connecting rod (146) being arranged to be actuated by the locking lever (128) to exert a clamping force on the rotating body (14), and the second connecting rod (148) being arranged to be actuated by the rotating body (14) to exert a clamping force on the frameset (93).

7. The surgical retractor fixing device according to claim 6, characterized in that the first connecting rod (146), the second connecting rod (148), the rotating body (14), and the locking lever (128) are arranged such that upon actuating the locking lever (128), first the first connecting rod (146) clamps the rotating body (14) to the clamp body (16) and after further actuating the locking lever (128) the second connecting rod (148) clamps the clamp body (16) to the frameset (93).

8. The surgical retractor fixing device according to claim 1, the fixing element (32) comprising a release element (58) for pivoting the bind plate (56) enabling the surgical retractor moving in the first and second directions.

9. The surgical retractor system according to claim 1, the surgical retractor including a shaft having a cylindrical shaped portion.

10. A surgical retractor system comprising:

at least one surgical retractor (12) and a surgical retractor fixing device (10) comprising:

a clamp body (16) arranged for removably fixing the surgical retractor fixing device (10) to a frameset (93) that extends along a frameset longitudinal axis (L) and that is arranged to be mounted to an operating table, and a rotating body (14) attached to the clamp body (16) being pivotable around an axis of rotation (A), the rotating body (14) comprising a fixing element (32) arranged for fixing a surgical retractor (12), where the fixing element is a releasable one-way fixing element (32), the rotating body (14) having a linear guide (36) transverse to the axis of rotation (A) for guiding the surgical retractor (12), and the fixing element (32) comprising a bind plate (56), the bind plate (56)

being pivotably attached to the rotating body (14) and at least partially surrounding the surgical retractor (12), the bind plate (56) pivoting with movement of the surgical retractor (12) in a first linear direction (d1) enabling movement of the surgical retractor (12) in the first linear direction along the linear guide (36), and the bind plate (56) resisting movement of the surgical retractor (12) in a second direction (d2) opposite the first linear direction.

11. The surgical retractor system according to claim 10, the clamp body (16) of the surgical retractor fixing device (10) having a mouth for at least partially encompassing the frameset (93), the mouth being open in a mouth direction (D), and the clamp body (16) comprising a locking device, the locking device having a locking rod (106) arranged for engaging with the frameset (93) thus fixing the clamp body (16) to the frameset (93) and a locking lever (128) arranged for actuating the locking rod piston (106), the locking lever (128) being pivotable around a locking lever swivel axis (S), the locking lever swivel axis (S) being substantially perpendicular to the frameset longitudinal axis (L) and to the mouth direction (D).

12. The surgical retractor system according to claim 11, where the locking rod comprises a first connecting rod (146) and a second connecting rod (148), the first connecting rod (146) being arranged to be actuated by the locking lever (128) to exert a clamping force on the rotating body (14), and the second connecting rod (148) being arranged to be actuated by the rotating body (14) to exert a clamping force on the frameset (93).

13. The surgical retractor system according to claim 12, where the first connecting rod (146), the second connecting rod (148), the rotating body (14), and the locking lever (128) are arranged such that upon actuating the locking lever (128), first the first connecting rod (146) clamps the rotating body (14) to the clamp body (16) and after further actuating the locking lever (128) the second connecting rod (148) clamps the clamp body (16) to the frameset (93).

14. The surgical retractor system according to claim 10, the fixing element (32) comprising a release element (58) for pivoting the bind plate (56) enabling the surgical retractor moving in the first and second directions.

15. A surgical retractor assembly comprising:

a frameset (93), the frameset (93) comprising an anchor element (162) for fixing the frameset (93) to an operating table, and at least one surgical retractor system (164) according to claim 10.

16. The surgical retractor system according to claim 10, the surgical retractor including a shaft having a cylindrical shaped portion.

17. A method of retracting structures in a surgical situation, the method comprising the steps:

mounting an anchor element (162) to an operating table, and attaching a frameset (93) to the anchor element (162), attaching a surgical retractor fixing device (10) to the frameset (93) comprising:

a clamp body (16) arranged for removably fixing the surgical retractor fixing device (10) to a frameset (93) that extends along a frameset longitudinal axis (L) and that is arranged to be mounted to an operating table, and a rotating body (14) attached to the clamp body (16) being pivotable around an axis of rotation (A), the rotating body (14) comprising a fixing element (32) arranged for fixing a surgical retractor (12), where the fixing element is a releasable one-way fixing element (32), the rotating body (14) having a linear guide (36) transverse to the axis of rotation (A) for guiding the surgical retractor (12), and the fixing element (32) comprising a bind plate (56), the bind plate (56)

being pivotably attached to the rotating body (14) and operable to at least partially surround the surgical retractor (12), the bind plate (56) pivoting with movement of the surgical retractor (12) in a first linear direction (d1) enabling movement of the surgical retractor (12) in the first linear direction along the linear guide (36), and the bind plate (56) resisting movement of the surgical retractor (12) in a second direction (d2) opposite the first linear direction, arranging a surgical retractor (12) relative to a human or animal patient, fixing the surgical retractor fixing device to the frameset (93), and moving the surgical retractor (12) along the linear guide (36), such that it retracts tissue or an organ of a patient.

18. The method according to claim 17, comprising the step actuating a release element of the surgical retractor (12) and thus releasing the tissue or the organ.

19. A surgical retractor fixing device comprising:

a clamp body (16) arranged for removably fixing the surgical retractor fixing device (10) to a frameset (93) that extends along a frameset longitudinal axis (L) and that is arranged to be mounted to an operating table, the clamp body (16) having a mouth for at least partially encompassing the frameset (93), the mouth being open in a mouth direction (D), and the clamp body (16) comprising a locking device, the locking device having a locking rod (106) arranged for engaging with the frameset (93) thus fixing the clamp body (16) to the frameset (93), and a locking lever (128) arranged for actuating a locking rod piston (106), the locking lever (128) being pivotable around a locking lever swivel axis (S), the locking lever swivel axis (S) being substantially perpendicular to the frameset longitudinal axis (L) and to the mouth direction (D), the locking rod comprising a first connecting rod (146) and a second connecting rod (148), the first connecting rod (146) being arranged to be actuated by the locking lever (128) to exert a clamping force on the rotating body (14), and the second connecting rod (148) being arranged to be actuated by the rotating body (14) to exert a clamping force on the frameset (93), and a rotating body (14) attached to the clamp body (16) being pivotable around an axis of rotation (A) the rotating body (14) comprising a fixing element (32) arranged for fixing a surgical retractor (12).

20. The surgical retractor fixing device according to claim 19, characterized in that the first connecting rod (146), the second connecting rod (148), the rotating body (14), and the locking lever (128) are arranged such that upon actuating the locking lever (128), first the first connecting rod (146) clamps the rotating body (14) to the clamp body (16) and after further actuating the locking lever (128) the second connecting rod (148) clamps the clamp body (16) to the frameset (93).

* * * * *